US012806357B2

(12) United States Patent
Kreutzer

(10) Patent No.: US 12,806,357 B2
(45) Date of Patent: Nov. 24, 2026

(54) RESPIRATORY INTERFACE WITH ACCESS PORTIONS

(71) Applicant: Christopher Andrew Kreutzer, Carrboro, NC (US)

(72) Inventor: Christopher Andrew Kreutzer, Carrboro, NC (US)

(73) Assignee: Christopher Andrew Kreutzer, Carrboro, NC (US)

( * ) Notice: Subject to any disclaimer, the term of this patent is extended or adjusted under 35 U.S.C. 154(b) by 279 days.

(21) Appl. No.: 18/357,122

(22) Filed: Jul. 23, 2023

(65) Prior Publication Data

US 2024/0075234 A1 Mar. 7, 2024

Related U.S. Application Data

(60) Provisional application No. 63/474,690, filed on Sep. 6, 2022.

(51) Int. Cl.
*A61M 16/06* (2006.01)

(52) U.S. Cl.
CPC ..... *A61M 16/06* (2013.01); *A61M 2205/0216* (2013.01); *A61M 2207/00* (2013.01); *A61M 2210/0618* (2013.01)

(58) Field of Classification Search
CPC .............. A61M 16/06; A61M 16/0605; A61M 16/0627; A61M 16/0666; A61M 2205/0216; A61M 2210/0618; A61M 2207/00; A62B 18/086; A41D 13/11–1146; A61F 2006/042
See application file for complete search history.

(56) References Cited

U.S. PATENT DOCUMENTS

| | | | | |
|---|---|---|---|---|
| 4,328,797 | A * | 5/1982 | Rollins, III | A61M 16/06 128/912 |
| 6,792,623 | B2 | 9/2004 | Luppi | |
| 9,981,104 | B1 * | 5/2018 | Groll | A61M 16/0694 |
| 11,020,557 | B1 * | 6/2021 | Lehman | A61B 5/082 |
| 2006/0054168 | A1 * | 3/2006 | Yu | A61M 16/06 128/206.28 |
| 2007/0193586 | A1 * | 8/2007 | Vaughn | A61F 6/04 128/844 |
| 2012/0285457 | A1 | 11/2012 | Mansour | |
| 2013/0172768 | A1 * | 7/2013 | Lehman | A61M 16/06 128/205.25 |
| 2019/0359303 | A1 * | 11/2019 | Shiue | B63C 11/12 |
| 2021/0274862 | A1 * | 9/2021 | King | A41D 13/11 |
| 2021/0299385 | A1 | 9/2021 | Wolf | |
| 2021/0345699 | A1 * | 11/2021 | Bush | A61B 90/40 |
| 2022/0023573 | A1 * | 1/2022 | Resto | A61M 16/0009 |
| 2022/0241622 | A1 * | 8/2022 | Mohanraj | A41D 13/1107 |
| 2022/0370746 | A1 * | 11/2022 | Kwok | A61M 16/06 |

* cited by examiner

*Primary Examiner* — Joseph D. Boecker

(57) ABSTRACT

A respiratory interface such as a CPAP mask comprises access portions. The access portions may comprise a compliant surface, such as a flexible or elastic membrane, configured to allow a user access to an irritated portion of the face, such as the nose, lips or cheeks. The membrane may be sized to allow a user's finger to reach the irritated portion. The access portions may allow a user to reach the irritated portion without waking up.

16 Claims, 9 Drawing Sheets

200

500

RESPIRATORY INTERFACE WITH ACCESS PORTIONS

CROSS-REFERENCE TO RELATED APPLICATIONS

This application claims the benefit of priority to U.S. provisional patent application No. 63/474,690, filed on Sep. 6, 2022, which is incorporated herein in its entirety by reference.

TECHNICAL FIELD

The embodiments provided herein relate to a respiratory interface, a ventilation device comprising the same, and to methods of manufacturing the respiratory interface.

BACKGROUND

Sleep apnea is a breathing disorder in which the breathing cycle may be interrupted during sleep. These interruptions may negatively impact the quality of sleep, resulting in physical and mental fatigue. Chronic sleep interruptions can also lead to more serious health problems, and the interruptions themselves are potentially life-threatening.

A common treatment for sleep apnea and other breathing disorders is the use of a ventilation device such as a continuous positive airway pressure (CPAP) system. In a CPAP device, the user may wear a respiratory interface, such as a mask, during sleep. The mask may cover, e.g., a user's nostrils or mouth in a sealed manner to create a chamber into which pressurized gas may be supplied.

SUMMARY

Embodiments of the present disclosure provide a respiratory interface comprising access portions. The respiratory interface may be a CPAP mask. The access portions may comprise a compliant surface, such as a flexible or elastic membrane, configured to allow a user access to an irritated portion of the face, such as the nose, lips or cheeks. The membrane may be sized to allow a user's finger to reach the irritated portion. The access portions may allow a user to reach the irritated portion without waking up.

Some embodiments of the present disclosure provide a method of forming a respiratory interface comprising access portions. The method may comprise forming a mask shell having access regions. The access regions may comprise apertures in the mask shell. The method may further comprise covering the access regions with a compliant material. The compliant material may have a rigidity lower than a rigidity of the mask shell. Some embodiments of the present disclosure provide a non-transitory computer-readable medium that stores a set of instructions that is executable by at least one processor of an apparatus to cause the apparatus to perform the above method.

BRIEF DESCRIPTION OF FIGURES

The above and other aspects of the present disclosure will become more apparent from the description of exemplary embodiments, taken in conjunction with the accompanying drawings.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations. Instead, they are merely examples of apparatuses and methods consistent with aspects related to the disclosed embodiments as recited in the appended claims. For example, although some embodiments are described in the context of a CPAP mask, the disclosure is not so limited. Other types of medical devices or sealed breathing apparatus may be used in some embodiments of the present disclosure.

Figure 1:
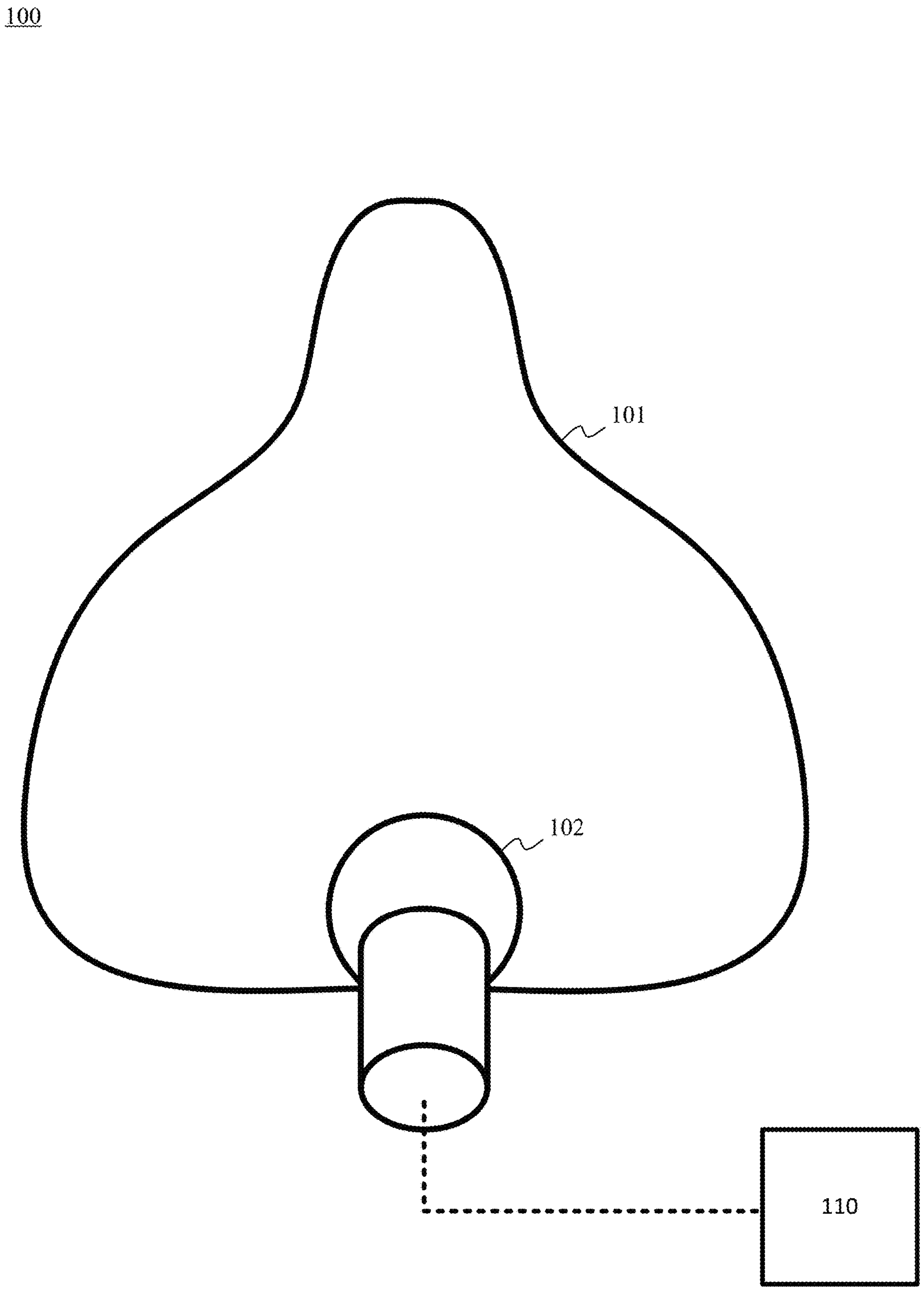
FIG. 1 is a schematic diagram illustrating an example respiratory interface according to a comparative embodiment.

FIG. 1 illustrates an example respiratory interface 100 according to a comparative embodiment. Respiratory interface 100 may comprise a mask shell 101 and supply coupling 102. Mask shell 101 may be formed of a rigid or a semi-rigid material. For example, mask shell 101 may be formed of, e.g., silicone, a thermoplastic polymer such as polycarbonate, or another plastic or other suitable material. In general, the material may have a sufficient rigidity to operate in a satisfactory manner under the range of pressure differentials created during supply of a pressurized gas to supply coupling 102. Mask shell 101 may be designed to enclose a portion of a user's face when worn, such as the mouth or nostrils, and created a substantially sealed breathing chamber.

Respiratory interface 100 may be configured for use in a ventilation device 110, such as positive airway pressure device, e.g., during sleep. Ventilation may be provided in continuous, bi-level, intermittent, or other forms. For example, respiratory interface 100 may be employed in a continuous positive airway pressure (CPAP) device. In a CPAP device, positive pressure may be maintained continuously in the airway throughout a respiratory cycle. Alternatively, the CPAP may operate in a bi-level positive airway pressure system, in which positive pressure may be maintained during inspiration but reduced during expiration. In an intermittent (non-continuous) positive pressure breathing (IPPB) system, pressure may be applied when an episode of apnea is sensed. In such procedures, a user may wear a mask, such as respiratory interface 100, over a breathing orifice during sleep, such the nose or mouth. Pressure from an air blower of ventilation device 110 may force air into a chamber formed by the mask shell 101 and through, e.g., the nasal passages. Typically, such masks may receive a gas supply line that delivers gas into the chamber. The walls are usually semi-rigid and have a face-contacting portion including an aperture that may be aligned with the patient's nostrils. The face-contacting portion can include a soft, resilient elastomeric material that can conform to various facial contours. The mask may be secured to the patient's head by straps. The straps may be adjusted to pull the mask against the face with sufficient force to achieve a gas tight seal between the mask and the patient's face but not so tight as to be uncomfortable. Gas is thus delivered to the mask and into, e.g., the user's nasal passages. Further information on CPAP mask and other respiratory devices may be found in: U.S. Pat. No. 7,845,352, which is herein incorporated by reference in its entirety; and U.S. Pat. No. 8,833,371, which is herein incorporated by reference in its entirety.

Conventional respiratory interfaces may be uncomfortable for a user to wear, making it more difficult for a user to achieve the uninterrupted sleep for which a ventilation device may be designed. For example, mask shell 101 may prevent the user from accessing a region of the face covered by the mask shell. If, for instance, the user's nose or mustache becomes irritated, the user may be unable to scratch or otherwise perform an adjustment to the irritated area without first dislodging the mask shell 101. When a user is sleeping without such a respiratory interface, the user may be able to quickly and easily remedy the irritation, such as by scratching the nose, without ever becoming awake. However, when a mask shell is secured tightly to a user's face, the effort required to dislodge it and access the irritated region may be enough to cause the user to awaken frequently. Choosing to ignore the irritation, on the other hand, can soon become a source of agitation that may also frequently interrupt a user's sleep, or cause the user to forego use of the ventilation device altogether.

Embodiments of the present disclosure may provide a respiratory interface comprising access portions. The access portions may comprise a compliant surface, such as a flexible or elastic membrane, configured to allow a user access to an irritated portion of the face, such as the nose, lips or cheeks. For example, the membrane may be sized to allow a user's finger to reach the irritated portion. The access portions may allow a user to reach the irritated portion with sufficient ease to perform an adjustment without waking up or with minimal disruption to sleep.

Relative dimensions of components in drawings may be exaggerated for clarity. Within the following description of drawings, the same or like reference numbers refer to the same or like components or entities, and only the differences with respect to the individual embodiments are described. As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

Figure 2:
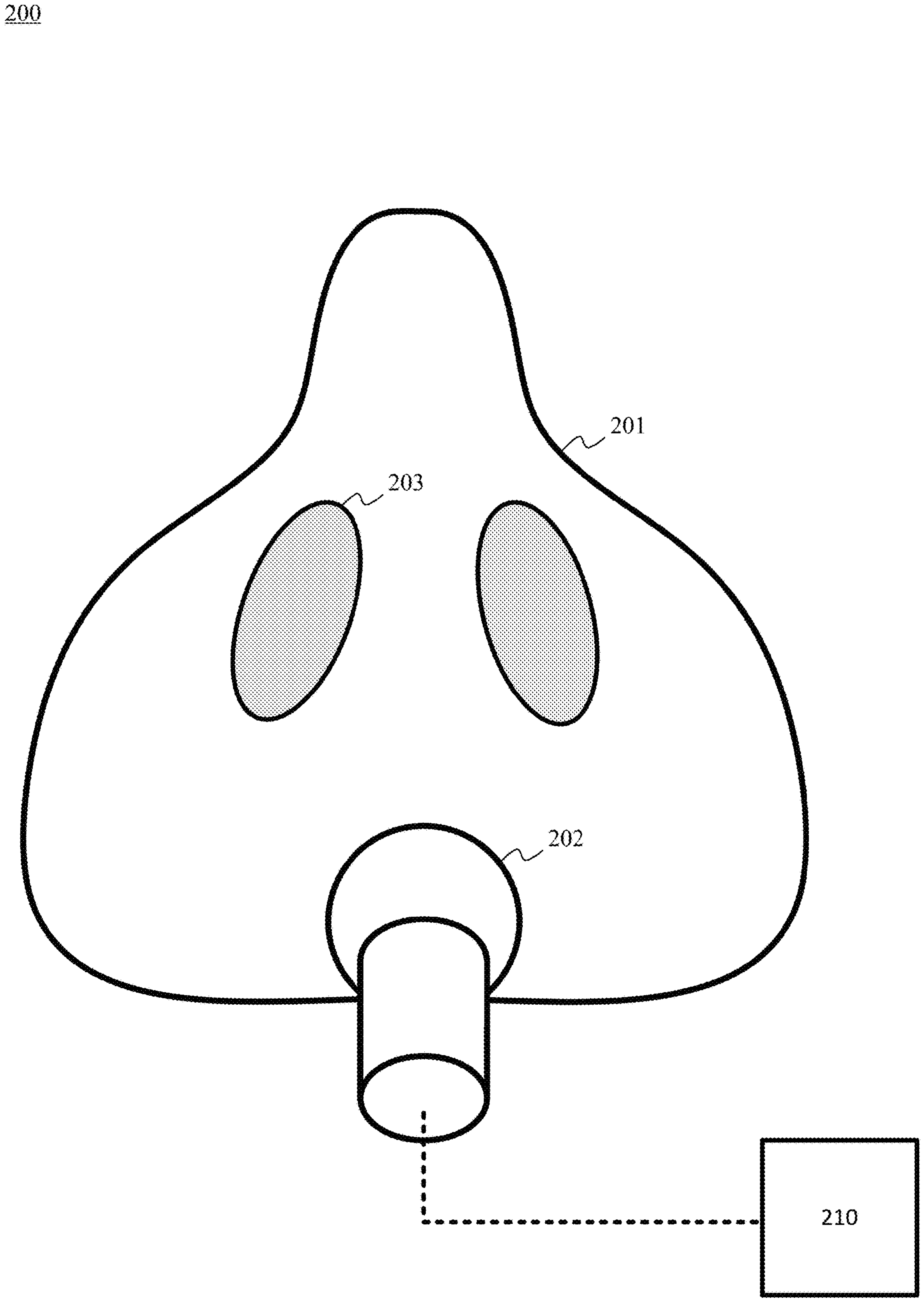
FIG. 2 is a schematic diagram illustrating an example respiratory interface, consistent with embodiments of the present disclosure.

FIG. 2 illustrates an example respiratory interface 200, consistent with embodiments of the present disclosure. Respiratory interface 200 may be similar to, e.g., respiratory interface 100 of the comparative embodiment, with the exception of the differences described below. In the appended drawings, similar elements may be labeled with corresponding numerals where the leading numbers are changed. For example, supply coupling 202 of FIG. 2 (as well as supply couplings 502 of FIG. 5 and 602 of FIG. 6) may be substantially similar to supply coupling 102 of FIG. 1. Respiratory interface may be configured for use with a ventilation device 210, for example, a CPAP, IPPB or other breathing device.

Respiratory interface 200 may comprise a mask shell 201. Mask shell 201 may be formed of a rigid or semi-rigid material. For example, the material may have a sufficient rigidity for the mask shell to operate in a satisfactory manner under the range of pressure differentials created during supply of a pressurized gas to supply coupling 202.

Respiratory interface 200 may further comprise a plurality of access portions 203. The access portions may be located, e.g., on a side face of mask shell 201. For example, access portions 203 may be placed in proximity to a nose region of a user of respiratory interface 200. Access portions 203 may be formed separately or integrally with mask shell 204. Access portions may be e.g., affixed with adhesive, or may be formed with a peripheral groove configured to engage with a lip of mask shell 204.

Access portions may have any size or shape. However, it may be desirable to configure access portions to be no larger than necessary so as to avoid the loss of structural integrity in mask shell 201. For example, in some embodiments, access portions may be sized to accommodate a typical human finger over a predetermined range of motion. Access portions 203 may comprise a membrane formed of a compliant material. The compliant material may have a lower rigidity than the material forming mask shell 201. The compliant material may be, e.g., a flexible material such as a polymer or an elastic material such as an elastomer. The membrane may be thin enough to allow tactile features of an intruding member to be felt. For example, the membrane may be thin enough to allow the contours of a fingernail at an outer side of the membrane to be felt on an inside of the membrane when pressed against a region of the face.

The compliant material may be configured to access a region of the face during use and remain in a substantially non-contact state from the face when not in use. For example, the compliant material may be sufficiently elastic to pull away from a user's face when an intruding member is not pressed against the membrane. Alternatively, the compliant material may be thin or flexible enough to be forced outward of the mask shell by gas pressure from ventilation device 210.

While two access portions 203 are shown, it should be understood that more or fewer than two are possible. For example, respiratory interface 200 may comprise a single centralized access portion 203, or may comprise, e.g., three, four, or more access portions.

Figure 3:
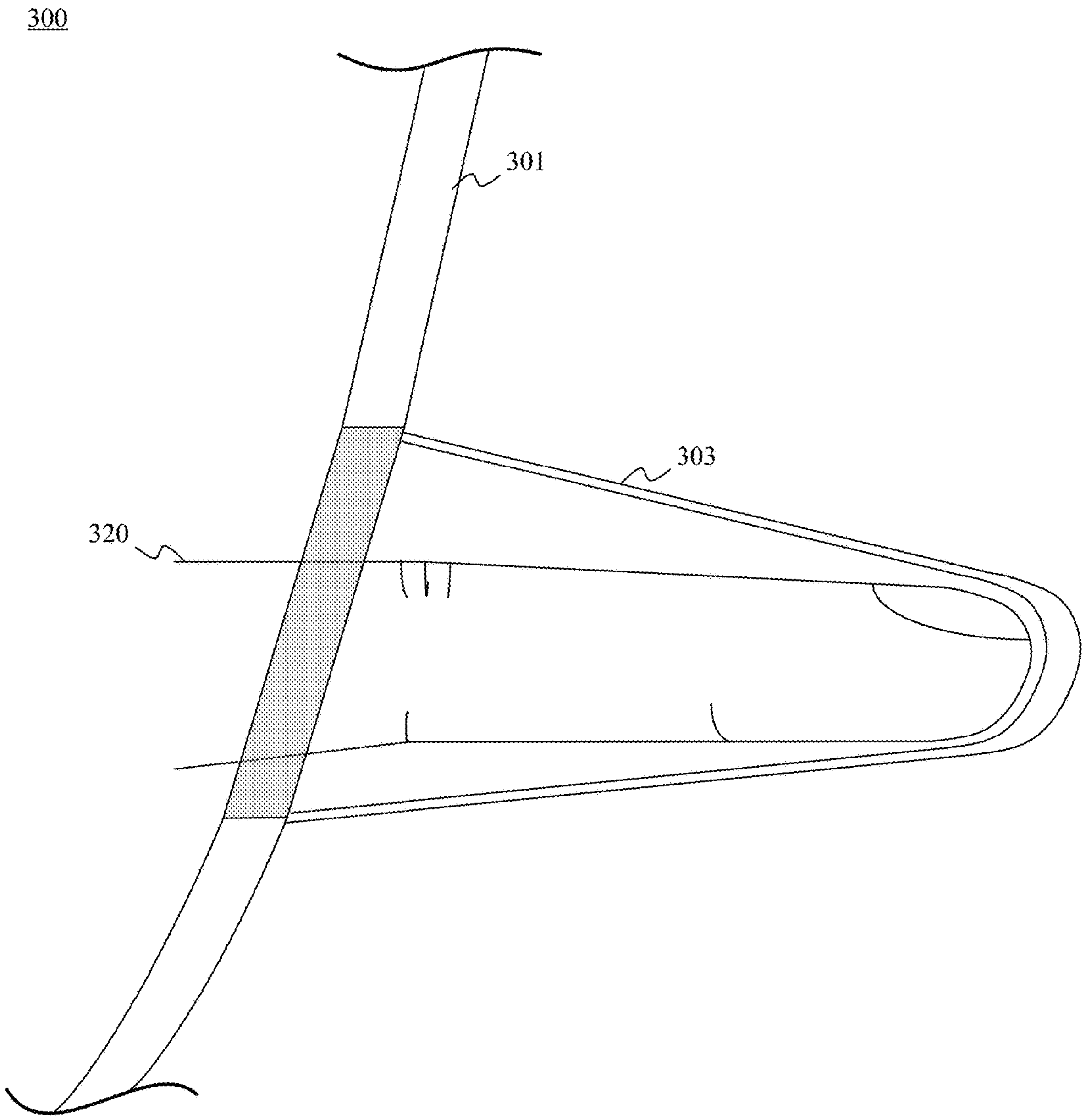
FIG. 3 is a schematic diagram illustrating an example respiratory interface, consistent with embodiments of the present disclosure.

FIG. 3 illustrates an example respiratory interface 300 during use, consistent with embodiments of the present disclosure. Respiratory interface 300 may be similar to, e.g., respiratory interface 200 of FIG. 2. In FIG. 3 a cross-section of a mask shell 301 and access portion 303 is shown along a portion of respiratory interface 300. An intruding member 320 such as, e.g., a user's finger or a scratching tool, may access the region inside a chamber formed by mask shell 301 by pressing against the membrane of access portion 303. In this way, a user may easily and comfortably make an adjustment during sleep, such as scratching the nose or lips, without dislodging mask shell 301 or losing gas pressure. When intruding member 320 is removed, the membrane of access portion 303 may withdraw from the face by, e.g., elasticity or gas pressure. The membrane of access portion 303 may have a substantially flat shape at rest. Alternatively, the membrane may have a curved surface. For example, the membrane may have a circular convex shape. As viewed in FIG. 3, the membrane may alternatively have a substantially finger-shaped surface curvature, such as a conic or cylindrical shape, or a shape resembling the finger of a glove.

Figure 4:
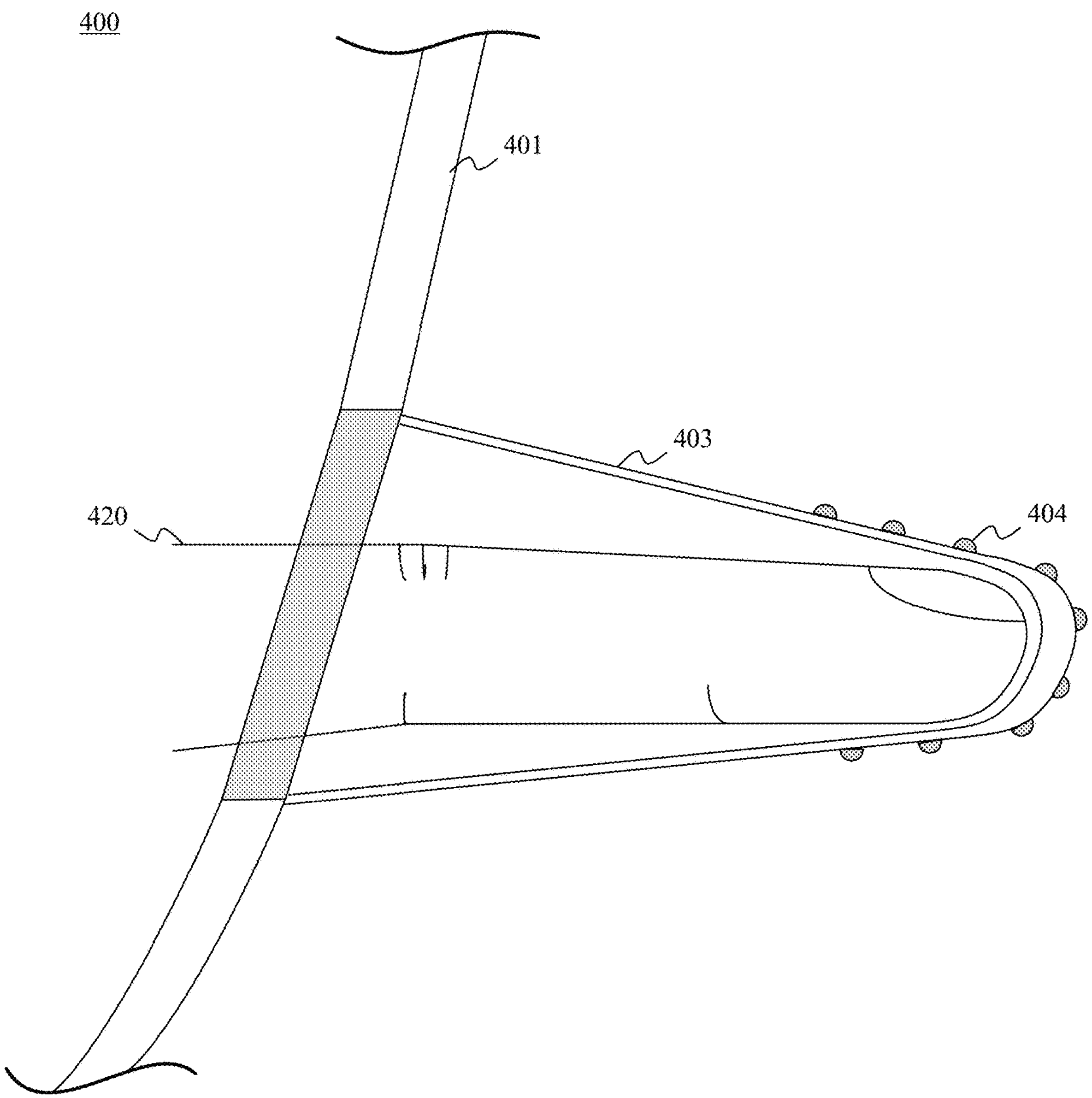
FIG. 4 is a schematic diagram illustrating an example respiratory interface, consistent with embodiments of the present disclosure.

FIG. 4 illustrates an example respiratory interface 400 during use, consistent with embodiments of the present disclosure. Respiratory interface 400 may be similar to, e.g., respiratory interfaces 200 of FIG. 2 or 300 of FIG. 3. In FIG. 4, the inner surface of access portion 403 may comprise abrasive elements 404. Abrasive elements 404 may be designed to provide improved scratching of an irritated region on a user's face. In some embodiments, the abrasive elements may be formed of, e.g., the same compliant material as the rest of the membrane of access portion 403. Alternatively, abrasive elements may comprise a harder material affixed to or embedded within the membrane of access portion 404. Abrasive elements 404 may take the form of nodules or lumps. Abrasive elements 404 may be dome shaped, pyramidal, plateau shaped, etc. Abrasive elements may comprise elongated pillars or bristles. Alternatively, abrasive elements may comprise a substantially continuous roughened surface over a portion of the inner surface of access portions 403. For example, the roughened surface may comprise an embossed pattern on an inner surface of access portions 403.

Figure 5A:
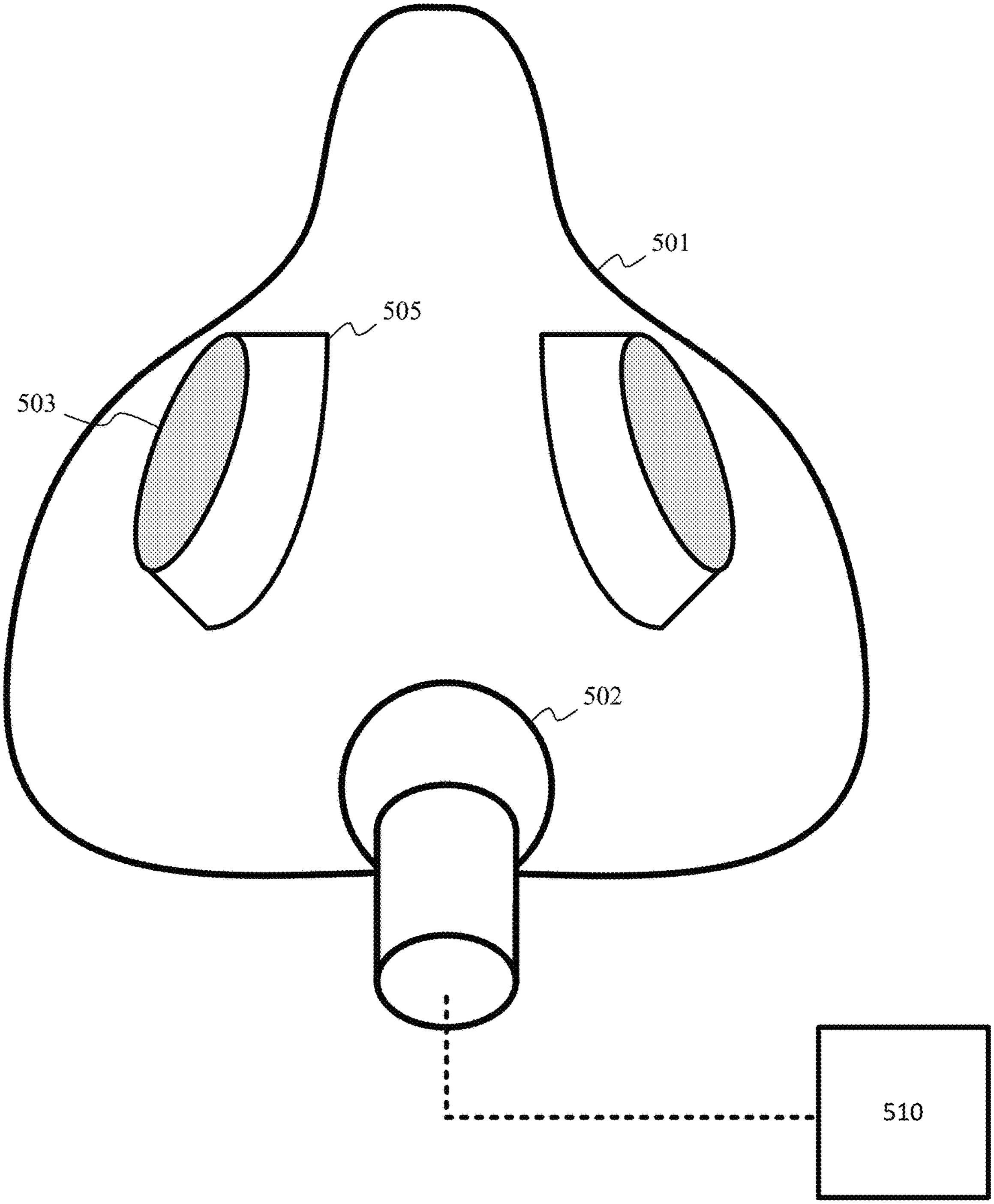
FIGS. 5A-C are schematic diagrams illustrating an example respiratory interface, consistent with embodiments of the present disclosure.
Figure 5B:
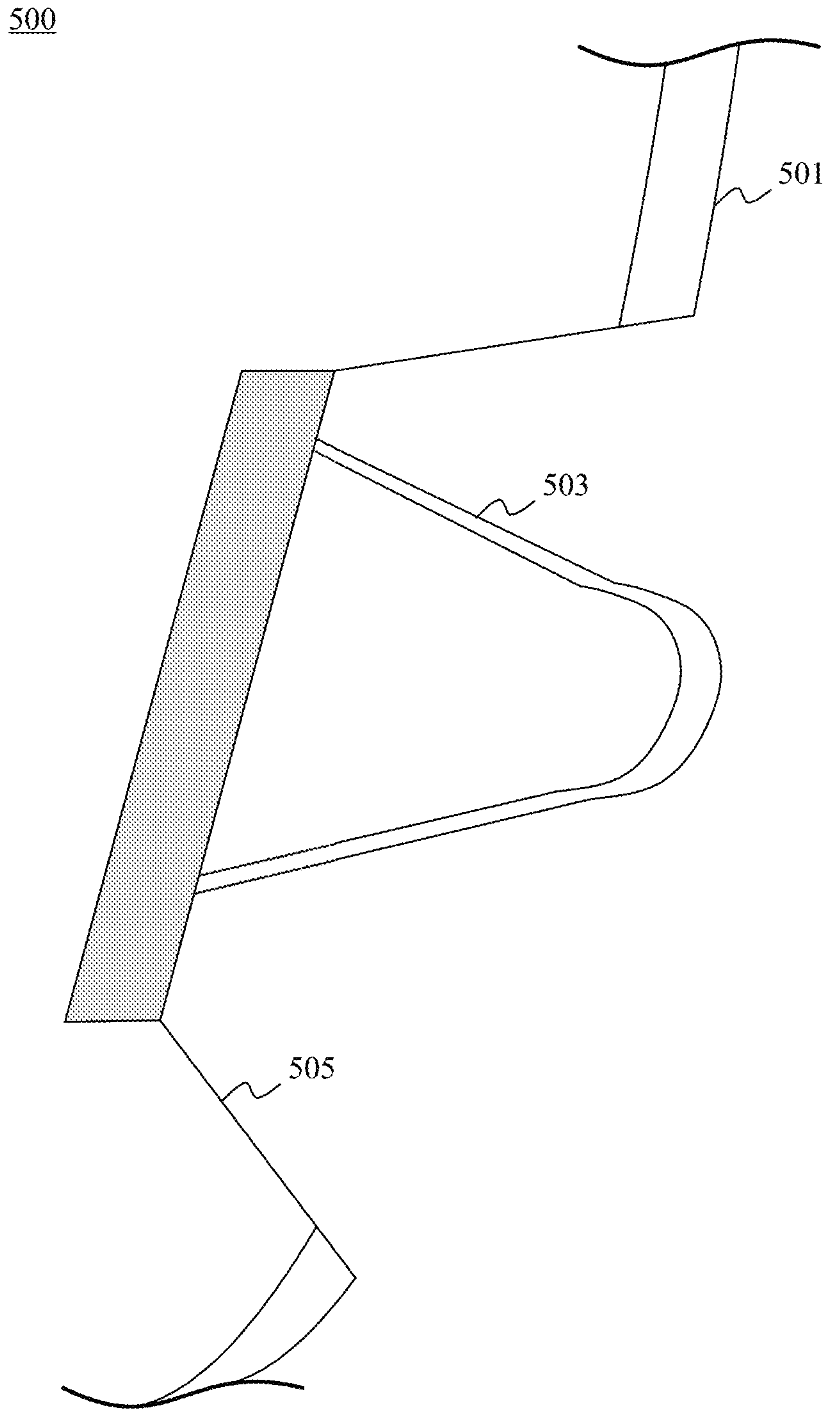
Figure 5C:
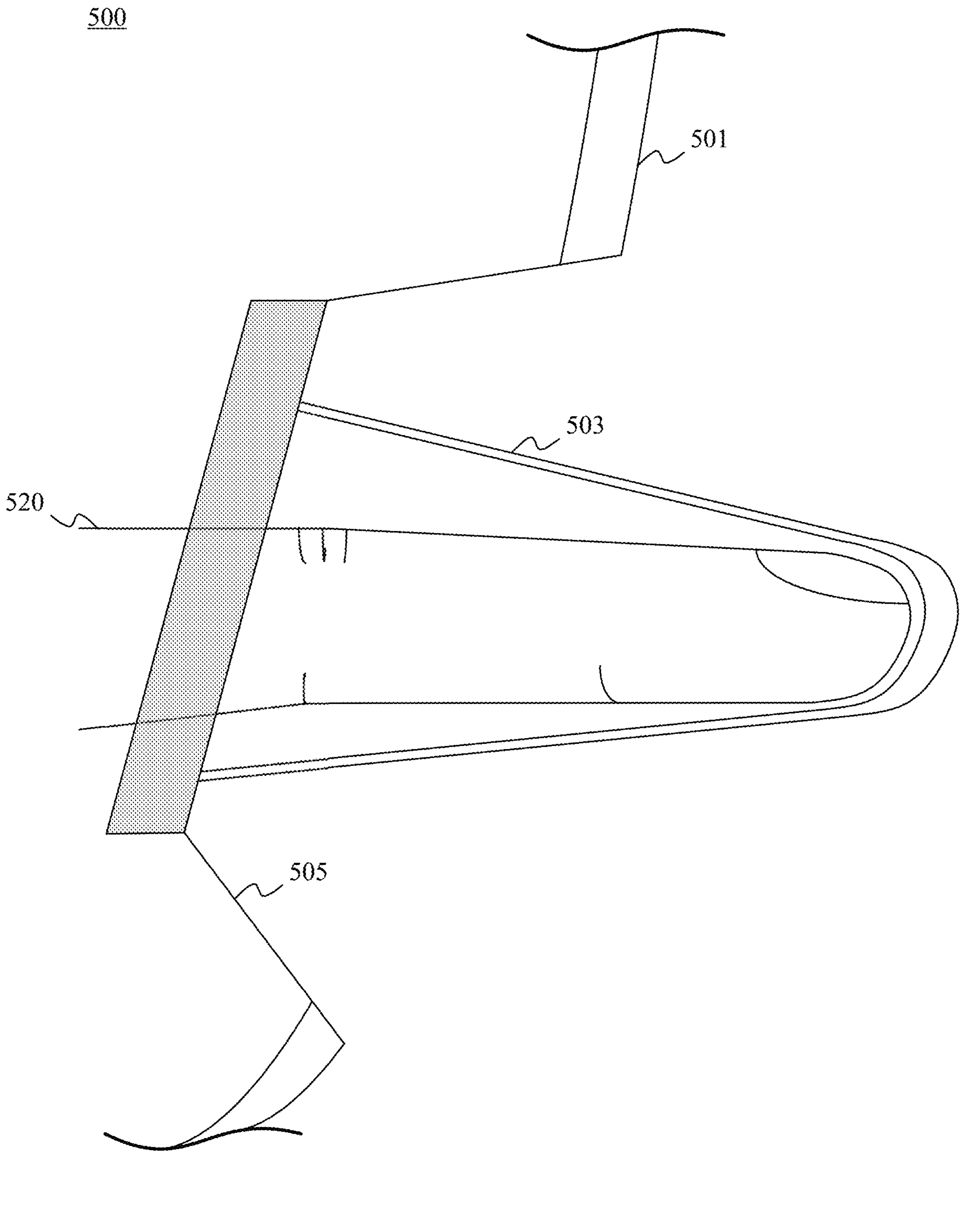

FIGS. 5A-5C illustrate an example respiratory interface 500 during use, consistent with embodiments of the present disclosure. Respiratory interface 500 may be similar to, e.g., respiratory interfaces 200 of FIG. 2, 300 of FIG. 3, or 400 of FIG. 4. In FIG. 5A, access portions 503 may distanced from a user's face by raised regions 505 on mask shell 501. In some embodiments, raised regions 505 may be formed integrally with mask shell 501, and may comprise the same material. Raised regions 505 may allow access portions 503 to be curved inward in a rest state without touching a user's face. For example, as seen in FIG. 5B, the access portion 503 is not in use by an intruding member 520. The access portion is at a rest state and may not extend far enough to touch a user's face. However, as seen in FIG. 5C, when intruding member 520 is inserted into access portion 503, access portion may be extended to touch the face. Raised regions 505 may allow greater design freedom in the surface contour of access portions 503 without the risk of bothering a user during sleep when the access portions are not in use.

Figure 6:
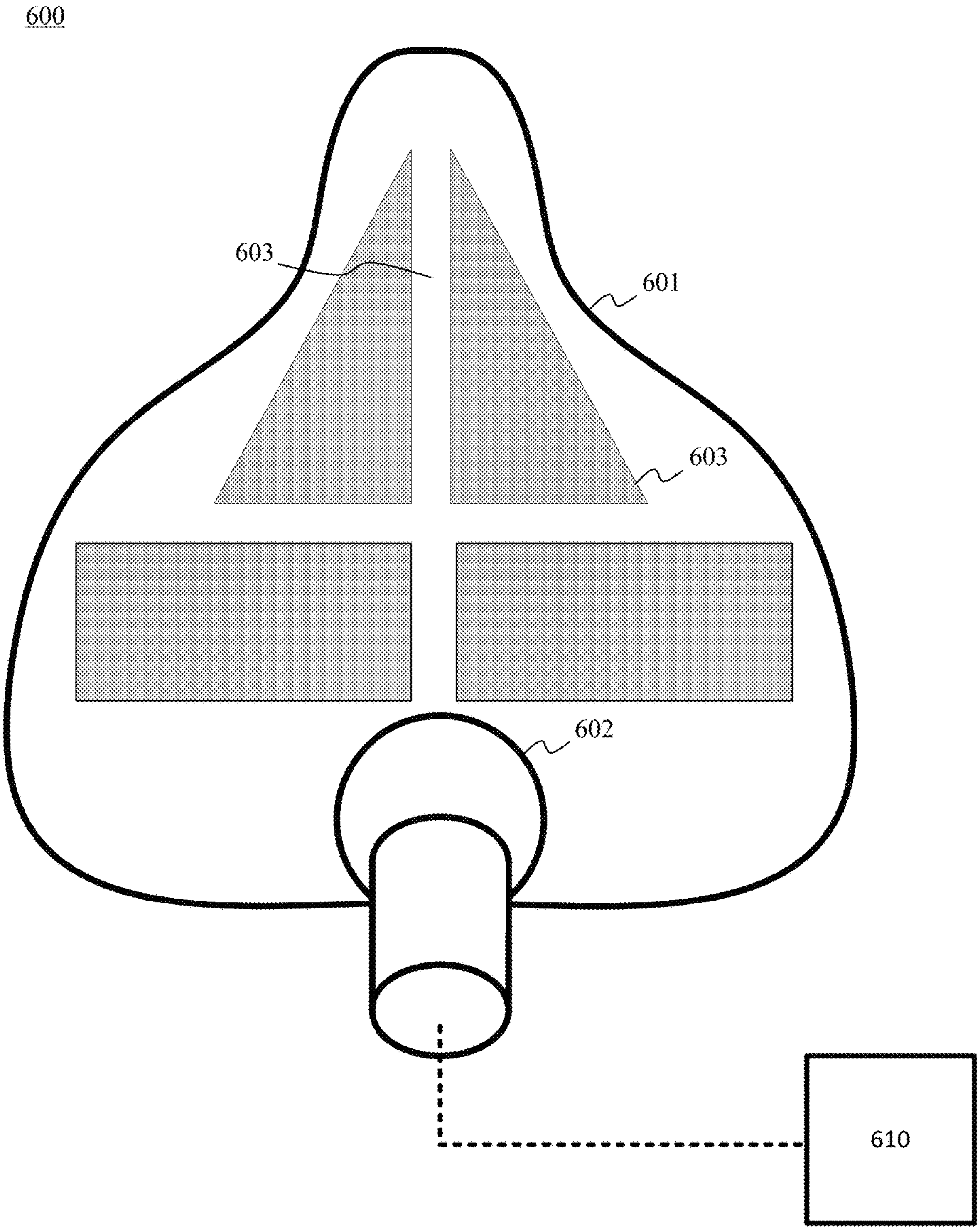
FIG. 6 is a schematic diagram illustrating an example respiratory interface, consistent with embodiments of the present disclosure.

FIG. 6 illustrates a further an example respiratory interface 600 during use, consistent with embodiments of the present disclosure. Respiratory interface 600 may be similar to, e.g., respiratory interfaces 200-500 of FIGS. 2-5 respectively. Mask shell 601 of respiratory interface 600 may take the form of, e.g., a skeletal frame onto which membranes of access portions 603 are attached. In some embodiments, a single membrane may cover an entire skeletal frame of mask shell 601, allowing for greater access to more regions of a user's face without sacrificing structural integrity of respiratory interface 600. In some embodiments, the skeletal frame of mask shell 601 may be formed of a highly rigid material, such as metal, dense plastics or ceramics.

Figure 7:
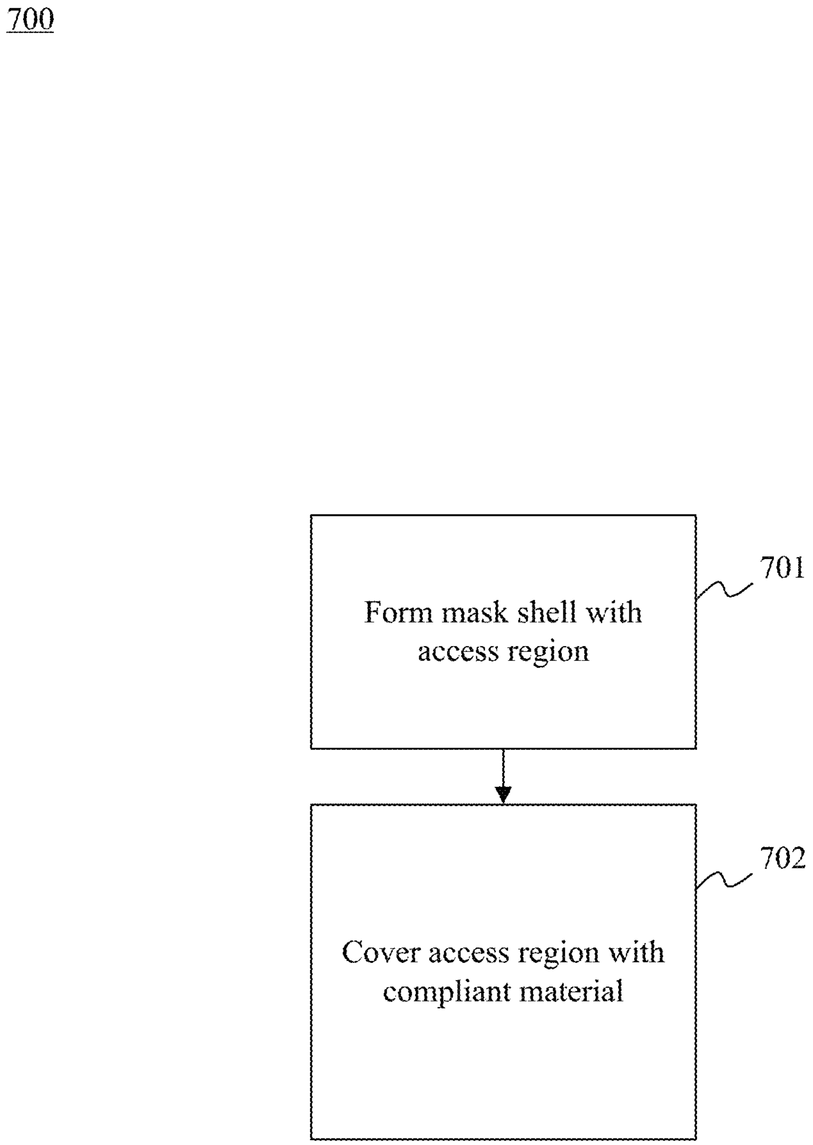
FIG. 7 is an example flowchart of a method of forming a respiratory interface, consistent with embodiments of the present disclosure.

FIG. 7 illustrates a method 700 of forming a respiratory interface, consistent with embodiments of the present disclosure. Method 700 may be used to form a respiratory device such as, e.g., any of respiratory devices 200-600 of FIGS. 2-6 respectively. At step 701 a mask shell is formed having an access region. For example, the mask shell may be formed by extrusion, injection molding or any other suitable manufacturing process. The mask shell may be formed with material initially omitted from the access region, or the access region may be formed later.

At step 702, the access region may be covered with a compliant material. For example, the material may be flexible or elastic. The compliant material may form an access portion. The access portion may be placed in proximity to a nose region of a user of the respiratory interface. The access portion may be formed separately or integrally with the mask shell. The access portion may be e.g., affixed with adhesive, or may be formed with a peripheral groove configured to engage with a lip of mask shell. The respiratory device may be used with, or form part of, a ventilation device such as a CPAP or IPPB device.

A non-transitory computer readable medium may be provided that stores instructions for a processor of a controller to carry out, among other things, a method of forming a mask as disclosed above, such as method 700. Common forms of non-transitory media include, for example, a floppy disk, a flexible disk, hard disk, solid state drive, magnetic tape, or any other magnetic data storage medium, a Compact Disc Read Only Memory (CD-ROM), any other optical data storage medium, any physical medium with patterns of holes, a Random Access Memory (RAM), a Programmable Read Only Memory (PROM), and Erasable Programmable Read Only Memory (EPROM), a FLASH-EPROM or any other flash memory, Non-Volatile Random Access Memory (NVRAM), a cache, a register, any other memory chip or cartridge, and networked versions of the same.

The embodiments may further be described using the following clauses:

1. A respiratory interface, comprising:
   a mask shell configured to cover a portion of a user's face; and
   an access portion configured to allow the user to access the portion of the user's face covered by the mask shell without removing the respiratory interface from the user's face.
2. The respiratory interface of clause 1, wherein the access portion comprises a compliant material.
3. The respiratory interface of clause 2, wherein the compliant material comprises an elastic material.
4. The respiratory interface of clause 1, wherein the access portion comprises a substantially finger-shaped surface curvature.
5. The respiratory interface of clause 1, wherein:
   the mask shell comprises a first material having a first rigidity;
   the access portion comprises a second material having a second rigidity; and the first rigidity is higher than the second rigidity.
6. The respiratory interface of clause 1, wherein the access portion comprises a plurality of abrasive elements formed on an inner surface of the access portion.
7. The respiratory interface of clause 6, wherein the plurality of abrasive elements comprises a roughened surface pattern.
8. The respiratory interface of clause 6, wherein the plurality of abrasive elements are formed from a same material as a membrane of the access portion.
9. The respiratory interface of clause 6, wherein the plurality of abrasive elements are formed from a material attached to or embedded within a membrane of the access portion.
10. The respiratory interface of clause 1, wherein the mask shell comprises a raised portion supporting the access portion.

11. The respiratory interface of clause 1, further comprising:
a second access portion,
wherein the first access portion is located on a first side face of the mask shell, and the second access portion is located on a second side face of the mask shell opposite the first side face.
12. The respiratory interface of clause 1, wherein
the covered portion of the user's face comprises the nose of the user's face; and
the access portion is configured to allow the user to access the nose the user's face by an intruding member.
13. A ventilation device, comprising:
a gas supply configured to supply pressurized gas; and the respiratory interface of clause 1.
14. The ventilation device of clause 13, wherein the ventilation device is one of a continuous positive pressure airway device (CPAP) and an intermittent positive airway pressure device (IPPB)
15. A method of manufacturing a respiratory interface, comprising:
forming a mask shell, the mask shell being configured to cover a portion of a user's face; and
forming an access portion, the access portion configured to allow the user to access the portion of the user's face covered by the mask shell without removing the respiratory interface from the user's face.
16. A non-transitory computer-readable medium that stores a set of instructions that is executable by at least one processor of an apparatus to cause the apparatus to perform a method comprising:
forming a mask shell, the mask shell being configured to cover a portion of a user's face; and
forming an access portion, the access portion configured to allow the user to access the portion of the user's face covered by the mask shell without removing the respiratory interface from the user's face.

Block diagrams in the figures may illustrate the architecture, functionality, and operation of possible implementations of systems, methods, and computer hardware or software products according to various exemplary embodiments of the present disclosure. In this regard, each block in a schematic diagram may represent certain arithmetical or logical operation processing that may be implemented using hardware such as an electronic circuit. Blocks may also represent a module, segment, or portion of code that comprises one or more executable instructions for implementing the specified logical functions. It should be understood that in some alternative implementations, functions indicated in a block may occur out of the order noted in the figures. For example, two blocks shown in succession may be executed or implemented substantially concurrently, or two blocks may sometimes be executed in reverse order, depending upon the functionality involved. Some blocks may also be omitted. It should also be understood that each block of the block diagrams, and combination of the blocks, may be implemented by special purpose hardware-based systems that perform the specified functions or acts, or by combinations of special purpose hardware and computer instructions.

It will be appreciated that the embodiments of the present disclosure are not limited to the exact construction that has been described above and illustrated in the accompanying drawings, and that various modifications and changes may be made without departing from the scope thereof. The present disclosure has been described in connection with various embodiments, other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A respiratory interface, comprising:
a mask shell configured to cover a portion of a user's face; and
an access portion configured to allow the user to access the portion of the user's face covered by the mask shell without removing the respiratory interface from the user's face;
wherein the access portion is surrounded by the mask shell and forms an enclosed cavity configured to be directable toward the user's face by an inserted intruding member without being passed through by the inserted intruding member; and
a supply coupling configured to receive a supply of pressurized gas.

2. The respiratory interface of claim 1, wherein the access portion comprises a compliant material.

3. The respiratory interface of claim 2, wherein the compliant material comprises an elastic material.

4. The respiratory interface of claim 1, wherein the access portion comprises a substantially finger-shaped surface curvature.

5. The respiratory interface of claim 1, wherein:
the mask shell comprises a first material having a first rigidity;
the access portion comprises a second material having a second rigidity; and
the first rigidity is higher than the second rigidity.

6. The respiratory interface of claim 1, wherein the access portion comprises a plurality of abrasive elements formed on an inner surface of the access portion configured to be directable toward the user's face when the respiratory interface is worn.

7. The respiratory interface of claim 6, wherein the plurality of abrasive elements comprises a roughened surface pattern.

8. The respiratory interface of claim 6, wherein the plurality of abrasive elements are formed from a same material as a membrane of the access portion.

9. The respiratory interface of claim 6, wherein the plurality of abrasive elements are formed from a material attached to or embedded within a membrane of the access portion.

10. The respiratory interface of claim 1, wherein the mask shell comprises a raised portion supporting the access portion.

11. The respiratory interface of claim 1, further comprising:
a further access portion,
wherein the access portion is located on a first side face of the mask shell, and the further access portion is located on a second side face of the mask shell opposite the first side face.

12. The respiratory interface of claim 1, wherein
the covered portion of the user's face comprises the nose of the user's face; and
the access portion is configured to allow the user to access the nose of the user's face by the inserted intruding member.

13. A ventilation device, comprising:
a gas supply configured to supply pressurized gas; and the respiratory interface of claim 1.

14. The ventilation device of claim 13, wherein the ventilation device is one of a continuous positive pressure airway device and an intermittent positive pressure breathing (IPPB) device.

15. A method of manufacturing a respiratory interface, comprising:

forming a mask shell, the mask shell being configured to cover a portion of a user's face;

forming an access portion, the access portion configured to allow the user to access the portion of the user's face covered by the mask shell without removing the respiratory interface from the user's face, wherein the access portion is surrounded by the mask shell and forms an enclosed cavity configured to be directable toward the user's face by an inserted intruding member without being passed through by the inserted intruding member; and forming a supply coupling configured to receive a supply of pressurized gas.

16. A non-transitory computer-readable medium that stores a set of instructions that is executable by at least one processor of an apparatus to cause the apparatus to perform a method comprising:

forming a mask shell, the mask shell being configured to cover a portion of a user's face;

forming an access portion, the access portion configured to allow the user to access the portion of the user's face covered by the mask shell without removing the respiratory interface from the user's face, wherein the access portion is surrounded by the mask shell and forms an enclosed cavity configured to be directable toward the user's face by an inserted intruding member without being passed through by the inserted intruding member; and forming a supply coupling configured to receive a supply of pressurized gas.

* * * * *